(12) United States Patent
Khosla et al.

(10) Patent No.: US 7,792,598 B2
(45) Date of Patent: Sep. 7, 2010

(54) SPARSE SAMPLING PLANNER FOR SENSOR RESOURCE MANAGEMENT

(75) Inventors: Deepak Khosla, Camarillo, CA (US); James Guillochon, San Diego, CA (US)

(73) Assignee: Raytheon Company, Waltham, MA (US)

( * ) Notice: Subject to any disclaimer, the term of this patent is extended or adjusted under 35 U.S.C. 154(b) by 816 days.

(21) Appl. No.: 11/787,135

(22) Filed: Apr. 13, 2007

(65) Prior Publication Data

US 2008/0250875 A1 Oct. 16, 2008

(51) Int. Cl.
G06F 19/00 (2006.01)
(52) U.S. Cl. .......................... 700/50; 700/28; 702/127
(58) Field of Classification Search .................. 700/50, 700/19, 28, 31, 35, 47, 57; 702/127; 703/13, 703/20; 706/2
See application file for complete search history.

(56) References Cited

U.S. PATENT DOCUMENTS

| | | | |
|---|---|---|---|
| 5,537,119 | A | 7/1996 | Poore, Jr. |
| 6,704,692 | B1 | 3/2004 | Banerjee et al. |
| 6,801,878 | B1 | 10/2004 | Hintz et al. |
| 6,907,304 | B1 | 6/2005 | Hintz et al. |
| 2004/0064438 | A1 | 4/2004 | Kostoff |
| 2005/0114023 | A1 | 5/2005 | Williamson et al. |
| 2006/0239336 | A1 | 10/2006 | Baraniuk et al. |

OTHER PUBLICATIONS

Hynes et al., Multi-Agent simulation For Assessing Massive Senosor Deployment, Jul. 2004, Battlefield Technolgy, vol. 7 No. 2 p. 1-7.*
Bertsekas, D.P., et al., "Rollout algorithms for stochastic scheduling problems," J. Heuristics, 5 (1) (1999) 89-108.
Hintz, K. J. et al., "Multi-process constrained estimation," *IEEE Trans. Man Systems Cybernet.* 21 (1991)237-244.
Hintz, K. J., "A measure of the information gain attributable to cueing," IEEE Signal Process. Mag. (Special Issue on Math. Imaging) 19 (5) (2002) 85-95.
Kalandros, M. et al., "Covariance Control for Multisensor Systems," IEEE Trans. Aerospace Electronic Systems, vol. 38, No. 4, 2002.
Kalman, R. E. "A New Approach to Linear Filtering and Prediction Problems," *Transactions of the ASME—Journal of Basic Engineering*, 82(D), 35-45, 1960.

(Continued)

*Primary Examiner*—Kidest Bahta
(74) *Attorney, Agent, or Firm*—Baker Botts L.L.P.

(57) ABSTRACT

A method and system of a sparse sampling planner uses a finite number of measurements to determine a track's expected intermediate kinematic and classification state for a specific sensor action. It uses the expected track state to compute a reward function. The expected states are further propagated for actions at the next time step to determine the next states and so on. The sampling becomes sparse and the reward function is discounted as one propagates further in time. This produces a state-action tree that is more top-heavy while providing greater accuracy at times closer to the decision point. By doing so, the planner creates a plan comprising a sequence of actions that result in the highest reward. By employing various heuristics to further prune the tree gives highly accurate results with significant savings in computational processor time.

25 Claims, 7 Drawing Sheets

OTHER PUBLICATIONS

Kastella, K., Discrimination Gain to Optimize Detection and Classification, IEEE Transactions on Systems, Man, and Cybernetics, Part A: Systems and Humans, vol. 27, No. 1, pp. 112-116, Jan. 1997.

Kearns, M. J., et al., "A Sparse Sampling Algorithm for Near-Optimal Planning in Large Markov Decision Processes," *Proceedings of the Sixteenth International Joint Conference on Artificial Intelligence*, T. Dean (Ed.), pp. 1324-1331, Morgan Kaufmann, 1999.

Kreucher, C., et al., "Efficient Methods of Non-myopic Sensor Management for Multitarget Tracking", 43$^{rd}$ IEEE Conference on Decision and Control, Dec. 14-17, 2004, Atlantis, Paradise Island, Bahamas, pp. 722-717.

Kreucher, C., et al., "Information-Based Sensor Management for Simultaneous Multitarget Tracking and Identification", General Dynamics Michigan Research & Development Facility, Ypsilanti, MI.

Krishnamurthy, V. et al., "Hidden Markov model multiarm bandits: a methodology for beam scheduling in multitarget tracking," IEEE Trans. Signal Process. 49 (12) (2001) 2893-2908.

Krishnamurthy, V., "Algorithms for optimal scheduling and management of hidden Markov model sensors," IEEE Trans. Signal Process. 50 (6) (2002) 1382-1397.

Malhotra, R., "Temporal considerations in sensors management," Proceedings of the IEEE 1995 National Aerospace and Electronics Conference, NAECON, vol. 1, Dayton, Oh, May 22-26, 1995, pp. 86-93.

McIntyre, G. A. et al., "An Information Theoretic Approach to Sensor Scheduling," Signal Processing, Sensor Fusion, and Target Recognition V. Proceedings of the SPIE—The International Society for Optical Engineering, vol. 2755, Orlando, FL, Apr. 8-10 1996, pp. 304-312.

Rudary, M., "A Sparse Sampling Planner for Sensor Resource Management", Signal Processing, Sensor Fusion, and Target Recognition, XV, Proceedings of the SPIE—vol. 6235, 6235A, (2006).

Schmaedeke, W., "Information Based Sensor Management," Signal Processing, Sensor Fusion, and Target Recognition II. Proceedings of the SPIE—The International Society for Optical Engineering, vol. 1955, Orlando, FL, Apr. 12-14 1993, pp. 156-164.

Schmaedeke, W. et al., "Event-averaged maximum likelihood estimation and information-based sensor management," *Proceedings of SPIE*, vol. 2232, Orlando, FL, 1994, pp. 91-96.

Schmaedeke, W. et al., "Information Based Sensor Management and IMMKF," Signal and Data Processing of Small Targets 1998: Proceedings of the SPIE—The International Society for Optical Engineering, vol. 3373, Orlando, FL, Apr. 1998, pp. 390-401.

\* cited by examiner

The sparse sampling algorithm estimates values by sampling future states to a depth $d$. The small white circles represent sampled states and the black circles represent actions.

|  | True Class | | |
|---|---|---|---|
|  | c1 | c2 | c3 |
| Declared Class d1 | 0.7 | 0.15 | 0.15 |
| d2 | 0.15 | 0.7 | 0.15 |
| d3 | 0.15 | 0.15 | 0.7 |

SPARSE SAMPLING PLANNER FOR SENSOR RESOURCE MANAGEMENT

RELATED APPLICATION

This non-provisional patent application is being filed concurrently with the non-provisional application entitled "METHOD AND SYSTEM FOR ADAPTIVE CLOSED LOOP RESOURCE MANAGEMENT", bearing application Ser. No. 11/786,906 which is incorporated by reference herein.

BACKGROUND OF THE INVENTION

1. Field of the Invention

The present invention relates to sensor scheduling methods and systems and more specifically, to long term (non myopic) scheduling based on multisensor measurements taken from a plurality of objects or targets.

2. Description of Related Art

Use of information-theoretic measures such as entropy for sensor management has been known for many years now. Hintz et al. references [10,11] use the Shannon entropy while Schmaedeke and Kastella, reference [12], have chosen to use Kullback-Leibler (KL) divergence as measure of information gain. Most of the literature is directed to managing sensors using information-theoretic measures to maximize kinematic information gain only, references [1-2]. This is done without any consideration for the current situation and system performance in that the goal is to get as much information as possible. Thus, it is an open-loop approach to manage sensors, references [1-4]. Also, some prior art exists in managing sensors for maximizing identification (ID) and search as well, references [3-4]. In all of these approaches, the idea is to pick the sensing actions that maximize the instantaneous expected information gain. Thus, these approaches are myopic in the sense that they maximize the immediate reward without consideration for future actions/rewards.

There is also some recent prior art in managing sensors for closed-loop control, but only based on kinematic need, reference [5]. This need is calculated based on the current kinematic track state and the desired kinematic accuracy. The sensor gains are calculated and sensors are scheduled based on the kinematic need and gain. No direction is provided on how to extend this work for general system problems.

Non-Myopic, Long-Term Planning

By contrast, long-term approaches have the potential to produce the best results, but the computation time required for even simple environments is enormous when compared to near-term myopic approaches. Several researchers have come up with solutions that provide approximate answers, references [6-9]. While these approximations improve computation time, they are still very computational intensive.

Another prior art approach for long-term planning has been proposed in a reference, [14]. This approach called sparse sampling considers a chain of actions up to a certain depth time when making a decision. The advantage over an exhaustive search is that this approach covers less and less of the action space as the algorithm looks farther ahead into the future. This makes sparse planning significantly faster than other long-term approaches that consider the action tree in its entirety. In an exhaustive search, the belief state grows exponentially with look-ahead depth. It grows as classes (i.e. decision points). For example, if there are three possible classes and there are five decisions to make before the depth time is reached, then the belief state will be $3^5$=243 entries long at the bottom of the action tree. An example of this approach is the sparse sampling algorithm in the cited reference [14] for Markov decision processes proposed by Kearns, Mansour, and Ng. This algorithm is exponential in the depth of the search tree and is not very applicable to practical problems. Additionally, their reward function is based on information gain in contrast to that used by the system and method of the present invention.

Accordingly, it is a primary object of the present invention to provide a method and system which provides a more accurate long-term sparse sampling planner.

SUMMARY OF THE INVENTION

The present invention overcomes the above disadvantages of the prior art by providing a method and system that uses a finite number of measurements to determine a track's expected intermediate kinematic and classification state for a specific sensor action. It uses the expected track state to compute a reward function. The expected states are further propagated for actions at the next time step to determine the next states and so on. The sampling becomes sparse and the reward function is discounted as one propagates further in time. This produces a state-action tree that is more top-heavy while providing greater accuracy at times closer to the decision point. By doing so, the planner creates a plan comprising a sequence of actions that result in the highest reward. By employing various heuristics to further prune the tree gives highly accurate results with significant savings in computational processor time.

As illustrated in a preferred embodiment of the present invention, multisensors are provided which observe a set of tracks. Each sensor can be set to operate in one of several modes and/or viewing geometries. Each mode incurs a different cost and provides different information about the tracks. Each track has a kinematic state that tracks, for example, position and velocity in two dimensions and each track has a discrete type wherein the sensors can observe either or both of these, depending on their mode of operation. The system and method of the present invention operates to maximize the average rate of information gain (i.e. the total information gain divided by cost). According to the teachings of the present invention, the overall measure of information gain is determined by combining the kinetic and identification information gains for all of the tracks.

In a preferred embodiment, the system and method of the present invention is incorporated in a centralized sensor resource management for providing long term planner control wherein a single decision node determines the sensor resource management plan and all the sensors make measurements in accordance with the plan. This assumes that the decision node has perfect information about track state, sensor models and costs, etc. A generative model is used by the system of the present invention to compute a value function for the entire state space.

Also, in accordance with the teachings of the present invention, a new reward concept is utilized which is based on the rate of information gain. This approximation is exact when the sequence of actions is deterministic and independent of intervening observations. That is, instead of searching a fixed number of decisions into the future, the system and method of the present invention searches until the total cost of actions reaches a given cost horizon. If the final action in the search would take the total cost beyond the desired horizon, then its reward and cost are scaled. Since this method still has an exponential running time, threshold techniques are utilized by the system to heuristically reduce the action set. In the preferred embodiment, each such technique requires that the one-step expected rate of gain be computed for each action.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION OF THE PRESENT INVENTION

Figure 1A:
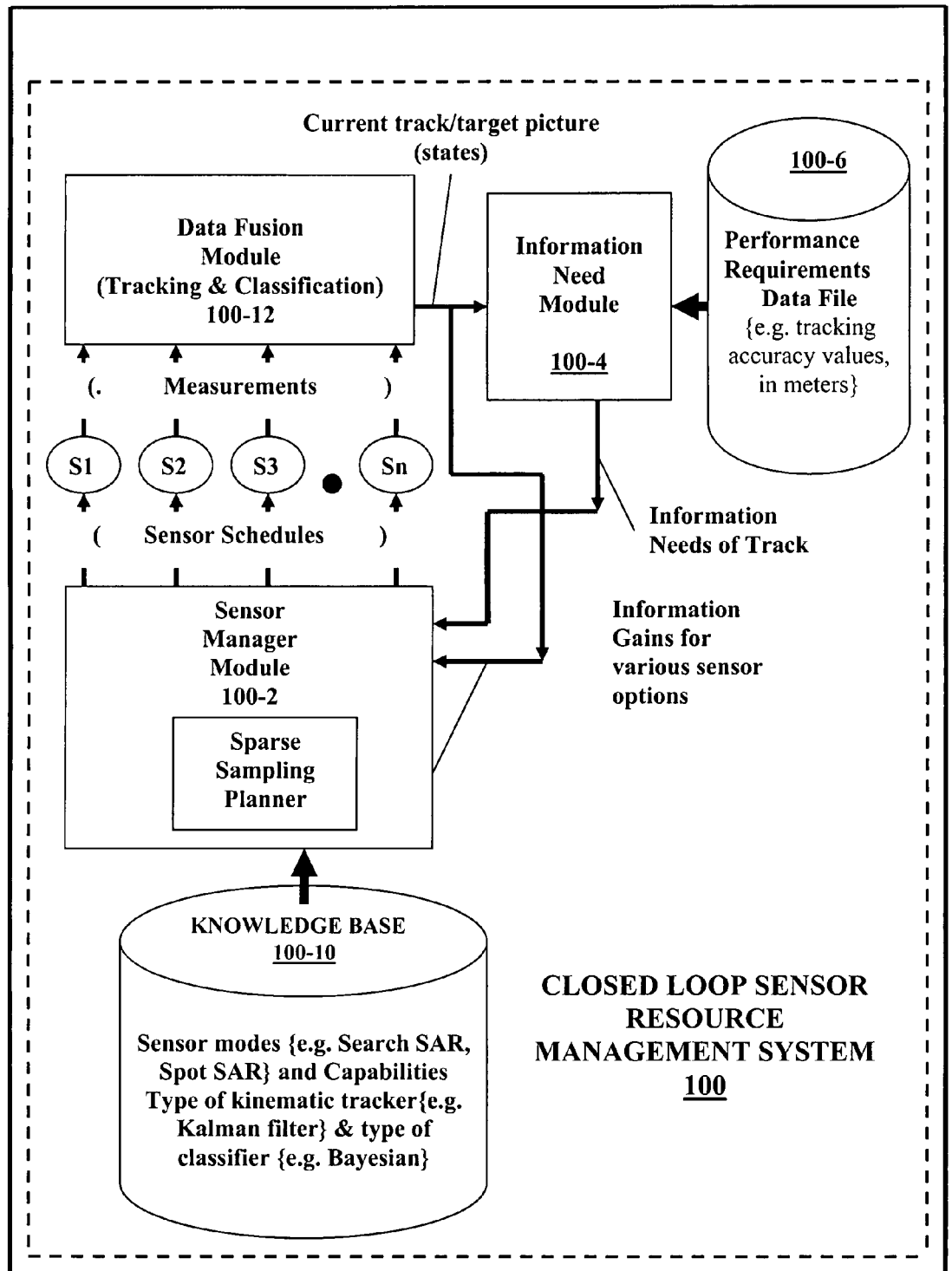
FIGS. 1a and 1b illustrate of a closed loop sensor resource management system which incorporates the sparse sampling system and method of the present invention.

FIG. 1a shows the closed loop sensor resource management system which uses a sparse sampling method and system incorporating the teachings of the present invention. In typical tracking and surveillance situations, the environment is comprised of a set of targets and their states. These target states can be divided into those targets that have not been detected and those targets that have been detected and are, or will soon be in "track". Targets that are in track have varying kinematic and identification accuracies. Targets that are not yet detected need more sensor search time to increase the chance of detection. Typically, the total area under search can be divided into sectors which are in turn subdivided into cells.

Before describing the preferred embodiment of the present invention, it will be noted that at the end of the specification, a glossary of terms has been included for the reader. These definitions are not intended to convey the full scope of the terms with respect to the present invention, but are provided to give the reader a general understanding of the terms and to serve as a central location to which the reader can refer.

Figure 1B:
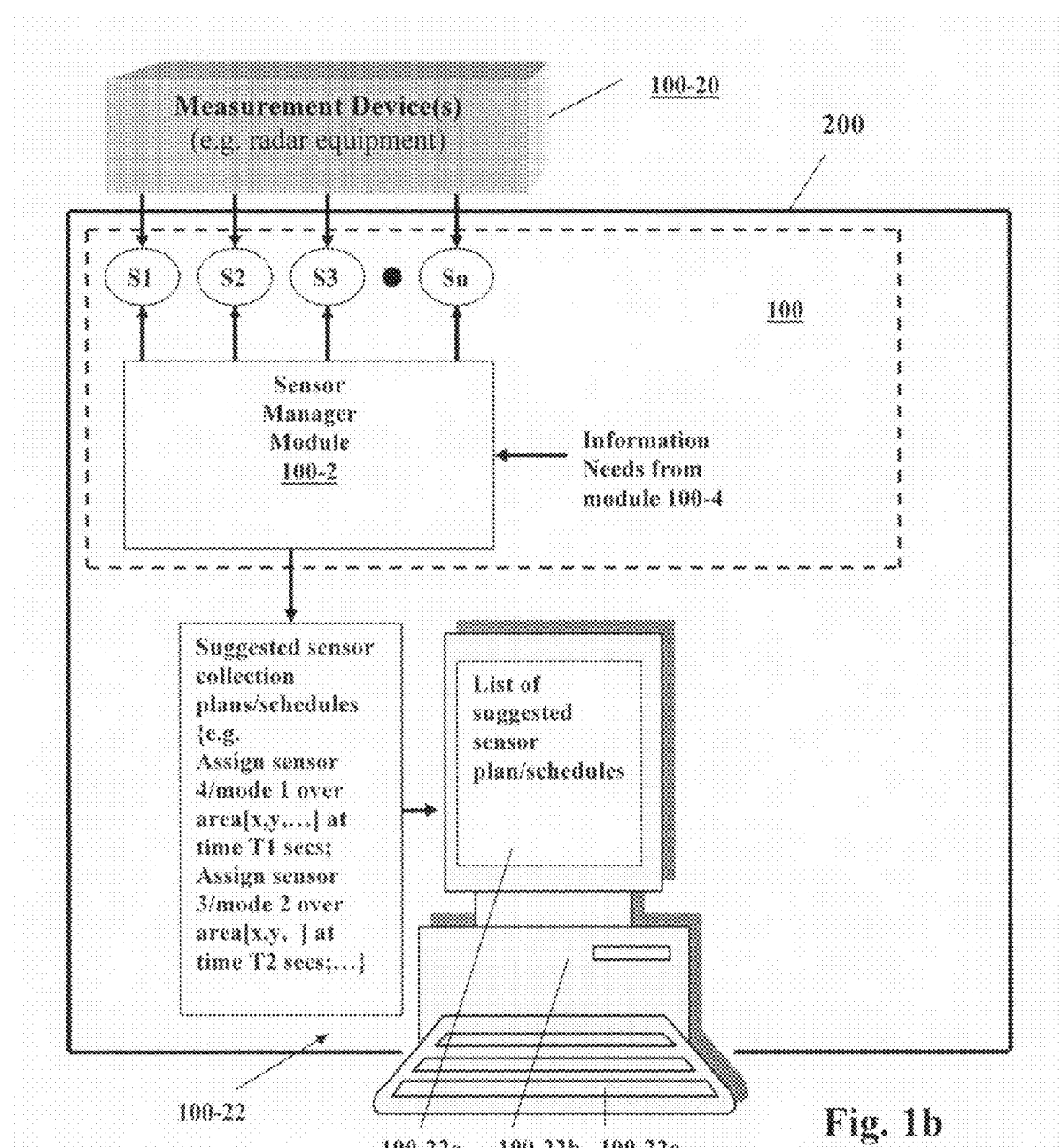

Description of FIGS. 1a and 1b

In greater detail, as illustrated in FIG. 1a, the system 100 includes a plurality of modules 100-2, 100-4, 100-8 and 100-12 which are operatively connected to form a closed loop sensor resource management system described in detail in the referenced related application. The system 100 forms part of a computer system 200 that includes a plurality of interconnected processors (not shown) that may be either general purpose or specialized for use with the system 100 that are programmed to carry out the functions of different ones of the modules 100-2 through 100-8. The necessary program instructions required to carry out the operations of the modules of system 100 are loaded or entered into the system 200 from disk such as file 100-6 or a workstation or other means well known in the art. The computer system 200 receives information from multiple sensors which it passes on to system 100 via its inputs such as multiple "ports".

As shown, a plurality of sensors represented as S1, S2, and S3 through Sn in FIG. 1a operatively couple to and is under the control of sensor manager module 100-2. The sensors S1 through Sn make measurements on the targets in a well known manner. It will be appreciated that the location of the sensors depends on the particular system application and hence is not relevant to understanding the teachings of the present invention.

Information need module 100-4 assesses the current system state and performance requirements or goals obtained by accessing a performance requirements data file 100-6 as shown in FIG. 1a. As discussed herein, the data file 100-6 contains requirements criteria previously established by an operator to be used assessing achievement of system performance goals. Also, the system 100 optionally provides feedback to the operator relative to the scheduled tasks being carried out. As shown in FIG. 1b, the operator is provided a list of suggested sensor plan/schedules by a sparse sampling planner component included in module 100-2 indicated.

In greater detail, as indicated in FIG. 1b, the workstation 100-22 is conventional in design and includes a keyboard 100-22a, a disk drive unit 100-22b and a monitor/display unit 100-22c. The keyboard 100-22a and disk drive unit 100-22b can be used for entering program instructions into the system 100. The display unit 22c as discussed is used for displaying task/option information received from sensor manager module 100-2.

The module 100-4 generates outputs indicating the information needs of the tracks which are applied as inputs to the Sensor Manager Module 100-2. As discussed herein, the sensor manager module 100-2 in turn generates output signals defining suggested sensor collection plans/schedules of sensor tasks.

In system 100, the output signals representative of suggested sensor collection plans/schedules generated by the sparse sampling planner component of module 100-2 correspond to commands (e.g. such as shown in FIG. 1b) that include parameters such as platform (sensor) number, task start time, mode type (e.g. search SAR, spot SAR and GMTI) and mode parameters (e.g. center coordinates of coverage area (patch) and coverage area (patch) size. An example of such commands is: Sensor S1: collect in GMTI mode over area X for the next T seconds; Sensor S2: Collect in search SAR mode over area Y, etc. Such commands may take the following form: Assign sensor 4/mode 1 over area {x, y, . . . } at time T seconds; Assign sensor 3/mode 2 over area [x, y, . . . ] at time T2 seconds; etc. Additionally, these commands could include:

A. Prioritized list of Needs tasks {e.g.,
  Track 1 Kinematic Need is X units;
  Track 2 Classification Need is Y units . . . }

B. Prioritized list of sensor options to satisfy needs tasks {e.g.,
  Track 1: Sensor 2 in Mode 3 is best option; Sensor 4 in Mode 1 is next best option, etc;
  Track 2: Sensor 1 in Mode 2 is best option . . . .

As shown in FIG. 1a, the sensors S1 through Sn operatively couple to data fusion module 100-12 which includes a Kalman filter network module and a Bayesian engine module. The module 100-12 receives sensor signals corresponding to kinematic and classification/ID measurements and using the Kalman filter network module takes kinematic measurements data and fuses them with the existing track state to create a new track state. The Bayesian engine module takes sensor classification measurements data and fuses them with the current classification state to produce a new classification state. As shown in FIG. 1a, signals representative of the current track states are applied as inputs to the information need module 100-4 which performs the operations discussed above.

Description of FIG. 1b

As indicated in FIG. 1b, the sensors S1 through Sn make measurements on the targets through measurement device equipment 100-20 (e.g. radar equipment) to which they operatively couple for receiving information signals. It will be appreciated that the location of such equipment 100-20 and sensors depends on the particular system application and hence is not relevant to understanding the teachings of the present invention. As discussed above, sensor manager module 100-2 generates via the sparse sampling planner incorporated therein, a list of actions included in suggested sensor/collection plans/schedules. These are provided to an operator via workstation 100-22 as previously discussed.

The different modules of the system 100 of FIG. 1 utilize Kalman Filter Networks and Bayesian networks for carrying out the functions of their associated modules. These networks are used for determining the kinematic state of each track and the identification/classification of the track. The following describes the application of these well known types of devices in generating the required signals during the carrying out of the different module functions.

Track State (Kinematic) The kinematic state of each track is modeled by a linear dynamical system and tracked with a Kalman filter network. It will be appreciated that it could be modeled by any generative model whose state can be estimated from observational data. The dynamics of the linear dynamical system are governed by the following equations.

$$X_t = \Phi X_{t-1} + w_t \quad (1)$$

$$w_t \sim N(0, Q) \quad (2).$$

Here, $X_t$ (i.e. a column vector) is the state of one of the tracks at time t. (If it is necessary to refer to the state of a particular track, i, a superscript t is added: $X_t^i$; the tracks are independent of each other) $\Phi$ and $Q$ are parameters of the system, and $N(m, \Sigma)$ denotes the multivariate normal distribution with mean vector m and covariance matrix $\Sigma$. If the track is observable at time t by sensor j (which depends on the state of the track and the action selected for the sensor), then a kinematic observation $(z_{t,j})$ is generated according to:

$$Z_{t,j} = H_{t,j} X_t + v_{t,j} \quad (3)$$

$$v_{t,j} \sim N(0, R_{t,j}) \quad (4).$$

wherein, $H_{t,j}$ determines what is measured by the sensor and $R_{t,j}$ is a measure of the accuracy of the measurement. $Z_t$ is defined to be the set (total) of all the kinematic observations of a track at time t.

Since the state of track t $(X_t)$ is unobservable, it must be estimated through the use of a Kalman filter network. The Kalman filter maintains a least-squares estimate $x(t|t) = E[X_t | Z_1, \ldots, Z_t]$ and a covariance matrix $P(t|t) = E[x(t|t)x^T(t|t) | Z_1, \ldots, Z_t]$ of the error. This is recursively maintained through the following sets of equations:

$$x(t|t-1) = \Phi x(t-1|t-1) \quad (5)$$

$$P(t|t-1) = \Phi P(t-1|t-1)\Phi^T + Q \quad (6)$$

$$P^{-1}(t|t) = P^{-1}(t|t-1) + \sum_{j=1}^{S} \chi_{t,j} H_{t,j}^T R_{t,j}^{-1} H_{t,j} \quad (7)$$

$$x(t|t) = P(t|t)\left(P^{-1}(t|t-1)x(t|t-1) + \sum_{j=1}^{S} \chi_{t,j} H_{t,j}^T R_{t,j}^{-1} z_{t,j}\right) \quad (8)$$

where $\chi_{t,j}$ is an indicator variable that is 1 when sensor j produces a kinematic observation of the track at time t and 0 otherwise.

Track State (Classification) As with the kinematic state, the identification of the track can be reasoned by applying Bayesian reasoning through the use of a Bayesian network. It will be appreciated that there are a number of other ways of implementing such reasoning. The sensors are modeled using confusion matrices. The klth element of $\Theta_{t,j}$ gives the probability at time t that sensor j reports the track as type k when it is type l. The uncertainty is modeled as a multinomial distribution; the kth element of the belief state b(t) is the belief (i.e. probability) at time t that the track is type k, given all the observations that have come up to (and including) time t. If the track is observable at time t by sensor j, then an identification observation $(o_{t,j})$ is produced. $O_t$ is taken to be the set of all of the identification observations of a track at time t.

Let $\Theta(o,t,j)$ be the diagonal matrix whose kkth element is the probability that sensor j would produce observation o at time t given that the track is of type k (i.e. the diagonal of this matrix is the oth row of $\Theta_{t,j}$). Then the belief state can be updated with the following equation:

$$b(t+1) = \left(\prod_{j=1}^{S} \Theta(o,t,j)^{\kappa_{t,j}}\right) \frac{b(t)}{\Gamma}. \quad (9)$$

where $\kappa_{t,j}$ is an indicator variable that is 1 when sensor j produces an identification observation of the track at time t and 0 otherwise, and $\Gamma$ is a normalizing constant (the elements of b(t+1) must add to 1).

Information Measure The measure defined here judges how much information is gained when transitioning from one state to another. To do this, the information gained about the (discrete) type as well as the (continuous) kinematic state is measured, and then they are weighed against each other. To measure information gained about the discrete type, Shannon entropy $h_s$ is used:

$$h_S(b(t)) = -\sum_{k=1}^{C} b_k(t) \log_2(b_k(t)). \quad (10).$$

The identification information gain is then $h_S(b(t)) - h_S(b(t+1))$. Similarly, the entropy in the kinematic state can be measured by the differential entropy $(h_d)$ of a normal distribution defined as follows:

$$h_D(P(t\mid t)) = -\frac{1}{2}((2\pi e)^K \det(P(t\mid t))). \quad (11)$$

Here, det(P) is the determinant of P; recall also that K is the dimension of the kinematic state of a track. As before, the kinematic information gain is given by $h_D(P(t\mid t))-h_D(P(t+1\mid t+1))$. In both the discrete case and the continuous case, it can be shown that the combined entropy of multiple tracks' state estimates is the sum of their individual entropies assuming, as in this case that the estimates for each track are independent of each other.

In order to get an overall measure of information gain, the information gains, kinematic and classification (identification), of all the tracks are combined as follows:

$$\Delta h(t) = \sum_{i=1}^{N}(h_S(b^i(t)) - h_S(b^i(t+1))) + \quad (12)$$
$$\alpha \sum_{i=1}^{N}(h_D(P^i(t\mid t)) - h_D(P^i(t+1\mid t+1))).$$

The parameter α can be used to trade off the importance of kinematic information gain and identification information gain. Each action (i.e. assignment of modes and viewing geometries to settings) has a deterministic cost that is known a priori; the cost at time t is written as $c_t$. The rate of information gain at time t is thus given by the following:

$$RIG(t) = \frac{\Delta h(t)}{c_t}. \quad (13)$$

Detailed Description of FIG. 1

Information Need Based on Performance Goals The metric and framework used by module 100-4 in computing information need for kinematic and classification established system performance requirements/goals and the disparate need results are then combined so as to bring them into a common framework or single metric.

Kinematic Information Need The module 100-4 determines the information need of each track when given track kinematic states based on desired kinematic performance requirements. The desired kinematic performance is usually specified in the form of tracking accuracy as for example, in terms of Circular Error Probable values (e.g. 5 m CEP).

This involves computing the differential entropy of a continuous random variable X with density f(x) where x is defined over a region I which can be viewed as a measure of system uncertainty or information state. The computing of differential entropy is described in detail in the related application.

In the Kalman filter incorporated into module 100-4, the state vector is assumed to be a normal random vector and covariance estimate at any time step (cycle) is a measure of the estimation uncertainty in the state vector. The entropy decreases with new measurements because the estimation uncertainty goes down. If the current state covariance matrix is denoted as $P_{before}$ and the desired covariance matrix by $P_d$ as specified by the performance requirements, then the desired information need is the difference between the current and desired entropies and is given as follows:

$$N_t(X) = H_{before}(X) - H_d(X) = \log_2\left(\frac{|P_{before}|}{|P_d|}\right). \quad (14)$$

It will be noted that desired information need $N_t$ output generated by module 100-4 is positive as long as the desired covariance has not been achieved. Thus, tracks with high $N_t$ values need kinematic sensor measurements urgently. Additionally, track priority $P_t$ provided as supplemental information can be lumped into track need as follows:

$$N_t(X) = P_t \log_2\left(\frac{|P_{before}|}{|P_d|}\right). \quad (15)$$

Equation (16) is a measure of the kinematic information need of a target (track). If it is assumed that there are T existing tracks, the need $N_t \forall_t = 1, \ldots, T$ of each track can be computed using Equation (16). As shown, the track priority, current covariance and desired covariance are used to compute the track kinematic information need.

Classification (Identification) Information Need The module 100-4 computes the information need of each track based on desired performance requirements (i.e. obtained from file 100-6 of FIG. 1a) in terms of entropy when given current track classification states. The desired classification performance requirement is usually specified in the form of probability of correct identification (ID) as for example, 98%:

It is assumed that at a given time instant, the target classification of a track t is given by a probability distribution $P=\{p(c_1), (p(c_2), \ldots p(c_M)\}$, where $p(c_j)$ is the probability that the correct class is $c_j$. Then, the current target classification entropy is:

$$H^t(C) = -\sum_{j=1}^{M} p(c_j)\log_2 p(c_j) \quad (16)$$

The desired performance requirement on track accuracy is stated as the "probability of correct ID". This requirement can be interpreted in terms of entropy in the several ways implementable by different embodiments which quantify performance requirements based on classification entropy. For example: (1) a first embodiment quantifies performance requirements wherein, the probability of correct ID PC of a target is the same as the posterior probability of the class (ID) of the class with highest probability determined by the system: (2) a second embodiment quantifies performance requirements wherein, if there is a fully characterized system where a function relating the probability of correct ID vs. the posterior probability of declared ID which is the probability of the class or ID with the highest probability is available, then the declared ID probability corresponding to $P_c$ can be obtained from this function (referred to as receiver operating curve or ROC; and (3) a third embodiment quantifies performance requirements wherein the probability of correct ID can be determined is as a measure of confidence.

For any of the above embodiments (interpretations), the desired classification information need $N_t(C)$ of a track t is the difference between the current and desired entropy:

$$N_t(C) = H_t(C) - H_{t,d}(C) \quad (17)$$

It should be noted that the $H_{t,d}(C)$ is really $H_d(C)$ with the added t subscript denoting track t. It will be noted that tracks with high $N_t$ values are in more urgent need of ID or attribute measurements. Track priority P provided by supplemental information additionally can be lumped into track need as follows:

$$N_t(C) = P_t(H_t(C) - H_{t,d}(C)) \quad (18).$$

Equation (18) is a measure of ID information need of a target (track). If there are T existing tracks, then the need $N_t, \forall t=1, \ldots, T$ is computed for each track by module 100-4 using Equation (18). It can be seen that the track priority, current classification entropy and desired classification entropy are all needed to compute the track classification information need.

Information Gain The information gain of a sensor is defined as the difference between the current information state and the predicted information state if the sensor were to make that measurement. The following describes methods used for computing information gain for the kinematic and classification measurement modes.

Figure 2:
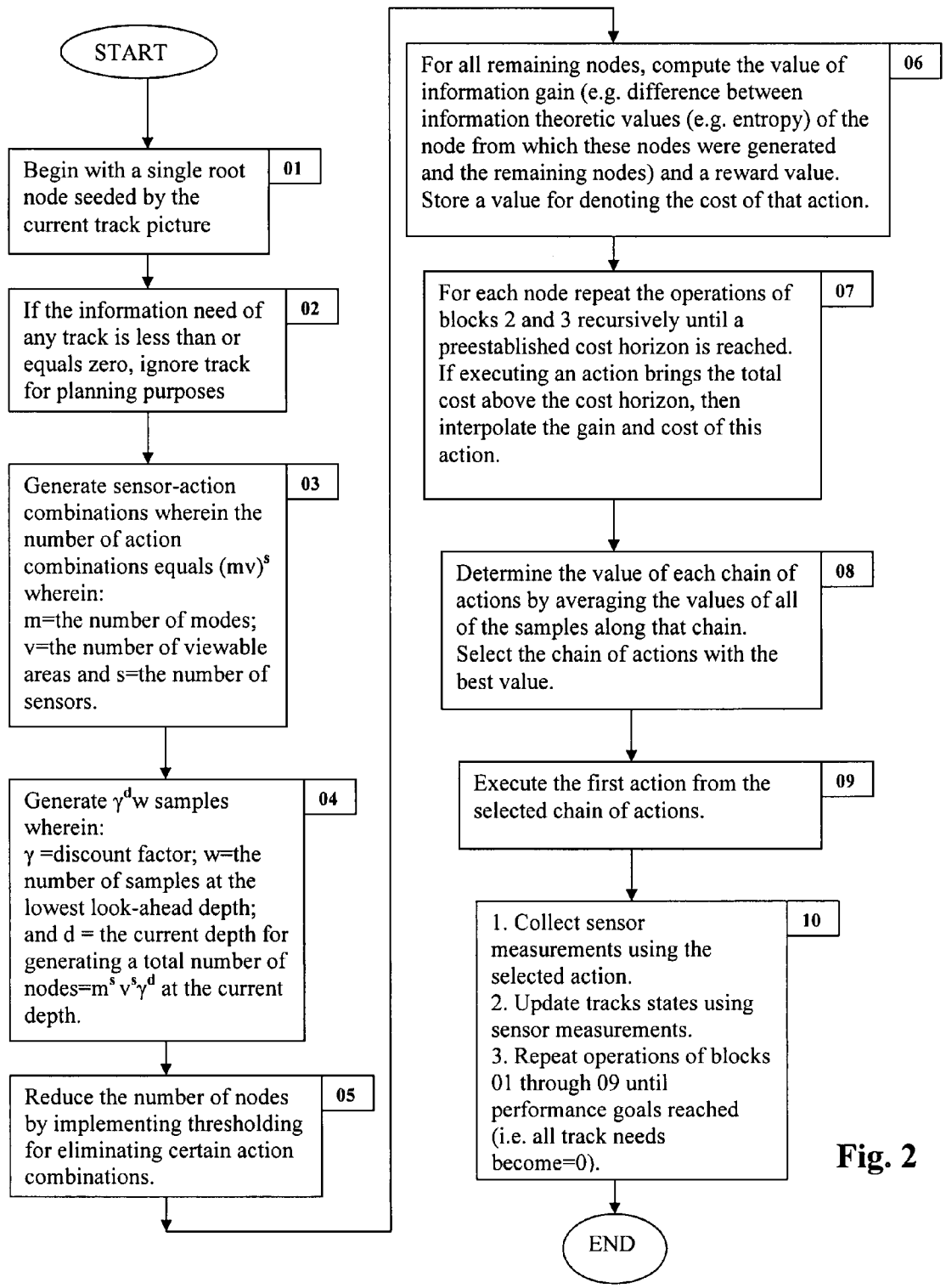
FIG. 2 is a flow chart illustrating the operation of the system and method incorporating the principles of the present invention.

Kinematic information gain As discussed herein relative to the flow chart of FIG. 2, the sparse sampling planner component of module 100-2 computes the information gain as the difference between the before and after entropies as follows:

$$I_{t,k}(X) = H_{before}(X) - H_{k,after}(X) = \log_2 \left( \frac{|P_{before}|}{|P_{k,after}|} \right). \quad (19).$$

The above equation gives a predicted measure of the utility of the sensor K for track t. It will be noted that the gain is computed before the sensor actually makes the measurement. Hence, it is a predictive computation. All sensors k with a positive value computed by module 100-2 from Equation (6) become options for satisfying the information need for track t. From this, a list of all such sensors for all tracks can be then computed and provided to an operator.

Classification information gain Similarly, the sparse sampling component of module 100-2 computes the classification gain wherein the information gain in classification for track t due the sensor k measurement using the following equation:

$$I_{t,k}(C) = H_t(C) - H_{t,k}(C/\text{measurement by sensor } k) \quad (20).$$

Again, the subscript t has been added to the above terms to denote track t. All sensors k with a positive value from Equation (7) become options for satisfying the information need for track t. A list of such sensors for all tracks can be then computed.

Sparse Sampling Planner Component of Module 100-2 As shown in FIG. 1, the sparse sampling component of module 100-2 receives the information needs outputs from module 100-4 and operates to generate the suggested sensor plans/schedules as represented in FIG. 1b. The basic sparse sampling value estimation method incorporating the teachings of the present invention is illustrated in FIG. 2.

The sparse sampling method of the present invention uses a well known method that employs a generative model to create sample trajectories. These are used to estimate state-action values and thereby to select an action. The generative model is a "black box" that takes a state (i.e. the state estimate and variance according the Kalman filter and the belief distribution over target types) and an action as input and generates observations and a reward as output according to the model's probability distributions. The state-action value at state s and action a (also known as Q(s, a)), is the expected value of starting from state s, taking action a, and thereafter acting according to an optimal policy. The well known sparse sampling method takes advantage of the fact that Q satisfies the Bellman equation which is as follows:

$$Q(s, a) = E_{s'} \left[ r(s, a, s') + \gamma \max_{a'} Q(s', a') \mid s, a \right] \quad (21).$$

Figures 3, 4:
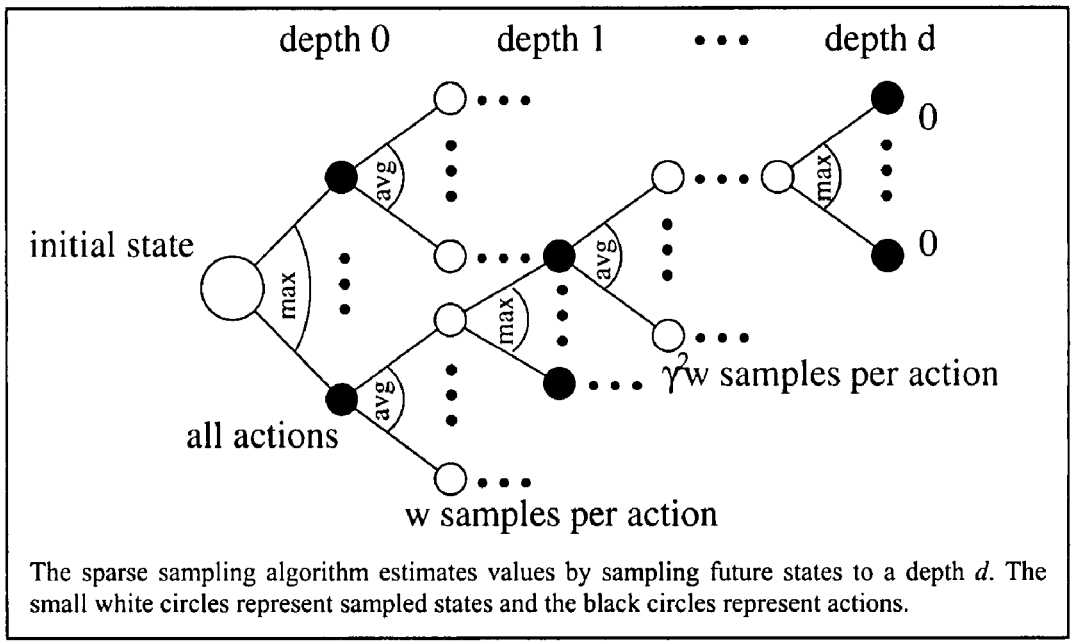
FIG. 3 is a diagram used in illustrating the sparse sampling method which employs the principles of the present invention.
FIG. 4 illustrates the simulation model architecture used in illustrating the principles of the present invention.

In this equation $\gamma \in [0, 1)$ is the discount factor, which determines how heavily the future is weighted (the return to be maximized at time t is $R_t = r_t + \gamma r_{t+1} + \gamma^2 r_{t+2} + \ldots$, where $r_t$ is the immediate reward/cost at time t). Sparse sampling uses a stochastic dynamic programming approach to estimate Q(s, a): take samples of the next state s' and reward r given s and a (using the generative model), then take the average of $r + \gamma \max_{a'} Q(s', a')$ over these samples. Of course, Q(s',a') must be estimated the same way. The accuracy of the Q estimates is determined by the number of samples taken at each depth and by the overall depth. The overall depth d and the number of samples taken for each action at the top level w are controllable parameters; the number of samples taken for each action at depth i is $\gamma^2$ times the number taken at depth i−1. The value estimation method described above is used to form the basis of a planning method of the present invention by selecting the action that maximizes the estimate of Q(s,a) for the initial state s. FIG. 3 illustrates the standard value estimation method which has been modified according to the teachings of the present invention.

The present invention uses a different reward concept than the prior art. In order to maximize rate, the sparse sampling planner component of module 100-2 computes a cumulative rate value by taking the ratio of cumulative reward to cumulative cost and allows for discounting by using the following reward measure:

$$R_t = \frac{r_t + \gamma r_{t+1} + \ldots}{c_t + \gamma c_{t+1} + \ldots}. \quad (22).$$

The appearance of $\gamma$ in both numerator and denominator of the equation (22) means that the present decision will be biased toward an action with high rate. If $\gamma$ appeared in the numerator only, then present decision would be biased toward an action with high reward (but possible high cost as well). It will be noted that the costs in equation (22) are constants for a given sequence of actions; thus, an expectation taken over $R_t$ can be computed by taking the expectation of the numerator and dividing by the constant denominator; this can be done recursively. However, when actions in the future depend on observations between now and then, $R_t$ is a quotient of random variables, so its expectations becomes uncertain and not recursively computable.

To avoid this problem, the expectations taken over $R_t$ is approximated with a different expectation as follows:

$$V_t = \frac{E[r_t] + \gamma E[r_{t+1} + \gamma r_{t+2} + \ldots]}{E[c_t] + \gamma \frac{E[r_{t+1} + \gamma r_{t+2} + \ldots]}{V_{t+1}}}. \quad (23).$$

This approximation is exact when the sequence of actions is deterministic and independent of intervening observations. Of course, the method of the preferred embodiment (described in pseudo code herein) further approximates by substituting sample averages for the expectations. It will be noted that the basic sparse sampling planner of the present invention instead of searching a fixed number of decisions into the future, searches until the total cost of actions reaches a given cost horizon. If the final action in the search would take the total cost beyond the desired horizon, then its reward and cost are scaled.

It will be appreciated that the sparse sampling method has an exponential running time wherein the generative model is called $O((wA)^d)$ times by the basic algorithm (letting A be the number of actions and ignoring the effect of reducing w by $\gamma^2$ at each level). Thus, the running time can be reduced significantly by restricting the size of the action space. Two simple thresholding methods are used to heuristically reduce the number of action combinations. Both methods require that the one-step expected rate-of-gain be computed for each action, as in a near term myopic planner.

The first thresholding method is n-best thresholding wherein only the n actions with the highest one-step expected rates-of-gain are considered. This reduces the number of calls to the generative model to $O((wn)^d)$. If n is 1, this is nearly equivalent to a near-term myopic planner. If there is a tie at the top-level, it is broken by the sparse sampling estimate of the Q value rather than arbitrarily.

The second thresholding method is $\alpha$ thresholding, wherein the $\alpha$ parameter controls which actions are considered. Let max be the maximum over all the actions of the expected one-step value, i.e. the expected rate-of-gain of the near-term planner. If max>0, those actions with expected one-step values at least $\alpha \times$max are considered; otherwise, the actions with expected one-step values of at least max/$\alpha$ are considered. The effect of $\alpha$ upon the running time is highly problem-dependent.

Pseudo Code for the Sparse Sampling Planner Component of Module 100-2

The following illustrates the implementation of the sparse planner method according to the present invention. This is given as an example, since it will be appreciated that many changes can be made to the different parameters given herein.

```
C-PLAN (γ, w, d, b)
{
  inputs: discount factor γ, sample width w, cost horizon d, initial state s
  outputs: the action to be taken (best) and the estimated discounted rate
    of that action (V), and the estimated discounted reward over the cost
    horizon of that action (R)
      if d ≦ 0 then return [nil, 0]
      for each action a:
        let avg[a] = 0
        let ravg[a] = 0
        repeat w times:
          let [o, r, c] = gen_model(s, a)
          if (d–c) > 0 then
            let s' = state_update(s, a, o)
            let [a', v', r'] = sparse_sampling_planner(γ,
  [γ²w], d–c, s')
            let c' = r' / v'
            let avg[a] = avg[a] + (r + γr') / ((c+γc')w)
            let ravg[a] = ravg[a] + (r + γr') / w
          else
            let avg[a] = avg[a] + r / (cw)
            let avg[a] = avg[a] + r / w
      let best = argmax_a avg[a]
      return [best, avg[best], ravg[best]]
}.
```

Description of Operation

With reference to the flow chart of FIG. 2, the operation of the preferred embodiment of the sparse sampling planner component of module 100-2 incorporating the principles of the present invention will now be described. As indicated in block 01, the sparse planner method begins with a single root node representative of the current state of the system comprising all of the tracks. The root node is "seeded" by the current track picture obtained from a single measurement of each target made by the sensors S1 through Sn.

As indicated in block 02, the kinematic and classification information need of each track is computed by information need module 100-4 of FIG. 1 in the manner described above. The output entropy information need values $N_t(x)$ and $N_t(C)$ are used by the planner component to generate a list of tracks and respective information need values. If the information need of any track is less than or equal to zero, then the listed track is ignored by the planner component as indicated in block 02.

As indicated in block 03, the planner component generates the number of possible sensor action combinations as a function of the number of sensor modes, number of sensors and the number of viewable areas wherein the total combinations equals $(mv)^s$. In generating the combinations, the planner component obtains sensor information characterstics for the particular sensor from knowledge base 100-10 of FIG. 1.

As indicated in block 04, the planner component generates a first or initial portion of a state-action tree which resembles the drawing in of FIG. 3. The generation of $\gamma^d$ samples produces a total number of nodes of the state-action tree having a current depth d with the number of samples w at the lowest look-ahead depth as indicated in block 04. Each sample becomes a new node in the sensor-action tree.

Next, as indicated in block 05, the planner component reduces the number of nodes of the state-action tree by performing one of the two thresholding (pruning) methods previously discussed. This results in the elimination of certain sensor-action combinations.

As indicated by block 06, for each of the remaining nodes of the portion of the state-action tree generated, the planner component computes the value of information gain in the manner described above (see equation 12) of each of the remaining nodes corresponding to the difference between the information gain value of that node and the node from which the node was generated. At this time, the planner component also computes the reward value defined as the rate of information gain (RIG) according to equation 13. For that node, the planner component stores the reward value and the cost of the action for that information gain computation. In this instance, cost can be viewed as being equal to time. For example, if a sensor mode requires a longer time, it is more costly. Also, other sensor characteristics could affect cost, such as sensor power, etc. These items are used by the system in defining the deterministic cost value.

As indicated by block 07, the operations of blocks 02 and 03 are repeated recursively resulting in the generation of additional layers or levels of the state-action tree. This continues until the planner component determines that a pre-established cost horizon has been reached. This ends or completes the state-action tree generation process by the planner component. As indicated in block 07, if the planner component determines that the execution of an action will bring the total cumulative cost above the cost horizon, then the planner component interpolates (scales) the gain and cost of this action.

Next, as indicated in block 08, the planner component traverses the value of each chain of actions along the state-action tree and averages the reward values of all the samples along the chain. The chain of actions having the best value is then selected by the planner component.

As seen from block 09, the sensor executes the first action from the selected chain of actions. As indicated in block 10, the system 100 collects the sensor measurements obtained as a result of executing the selected action. The fusion module 100-12 updates the current tracks states using the sensor measurements. The planner component of module 100-2 repeats the operations of blocks 01 through 09 until the performance goals are reached wherein all track needs become equal to zero.

From the above description, it is seen how the method and system uses a finite number of measurements to determine a track's expected intermediate kinematic and classification state for a specific sensor action. It uses the expected track state to compute a reward function. The expected states are further propagated for actions at the next time step to determine the next states and so on. The sampling becomes sparse and the reward function is discounted as one propagates further in time. This produces a state-action tree that is more top-heavy while providing greater accuracy at times closer to the decision point. By doing so, the planner creates a plan comprising a sequence of actions that result in the highest reward. By employing various heuristics to further prune the tree gives highly accurate results with significant savings in computational processor time.

Simulation Examples

Sensor model: A first simulation was performed wherein it was assumed that system 100 used two sensors that could operate in two modes each: a kinematic measurement mode (Mode 1) and a class measurement mode (Mode 2). It was also assumed that the sensor measurement errors are fixed (i.e., independent of target position, range, etc.). This a simplistic sensor model, was chosen to demonstrate the sensor resource management algorithms for maximizing both kinematic and classification accuracies simultaneously. The measurement accuracies and cost of these modes was as follows: For sensor 1, mode 1 provided position measurement with a variance of 0.01 m² and a cost of 2 units. Mode 2 provided class information with a cost of 1 unit. This mode was modeled as a confusion matrix with $P_c$ (Probability of correct class declaration)=70% and $P_f$ (Probability of incorrect class declaration)=30% (with equal errors on the each of the 2 incorrect classes, i.e., 15%) It was assumed that the sensors characterization was available in the form of completely specified conditional probabilities. This confusion matrix Ml of sensor 1 was represented as shown in FIG. 4.

For sensor 2, the modes had the same measurement accuracies and confusion matrix as sensor 1. However, the costs were reversed, i.e., mode 1 had a cost of 1 unit while mode 2 had a cost of 2 units. Sensors in both environments picked a track to observe at each decision point, and each sensor picked one of several modes available to it. In the "all visible" environment, all tracks were visible at all times, while the "blind spot" had one or more of the tracks pass through an area where they were not visible to any of the sensors.

Kinematic and Classification updates: A standard Kalman filter approach with a fixed measurement rate and no measurement delay was used as the tracking algorithm. A standard Bayesian classifier was used to update classification probabilities based on current state and sensor measurements. The simulation started with complete class ignorance for both targets, i.e., uniform prior distribution over these classes.

Planners: The simulation ran three different planners: a random planner, near-term planner and long-term planner constructed in accordance with the teachings of the present invention. Each planner determined which sensor in what mode should be assigned to which track at each sampling instant. Thus, the sensors picked a track to observe at each decision point, and each sensor picked one of several modes available to it. For the random planner, the simulator randomly picked a track with finite information need and paired it with a randomly chosen sensor (and a randomly chosen mode) which was not busy. The near-term planner maximized the instantaneous expected information gain. To do this, it evaluated each assignment of actions to sensors/modes (such an assignment termed called a joint action) by computing the expected classification information gain and kinematic information gain for each track given the joint action. For these scenarios, the size of the joint action space was 4×4 or 16 (each track can be assigned a sensor/mode pair giving 4 possible assignments). The long-term planner included the method of the present invention described earlier. For the long-term centralized parameters, there was no discount factor and the depth was 4 units.

Figure 5A:
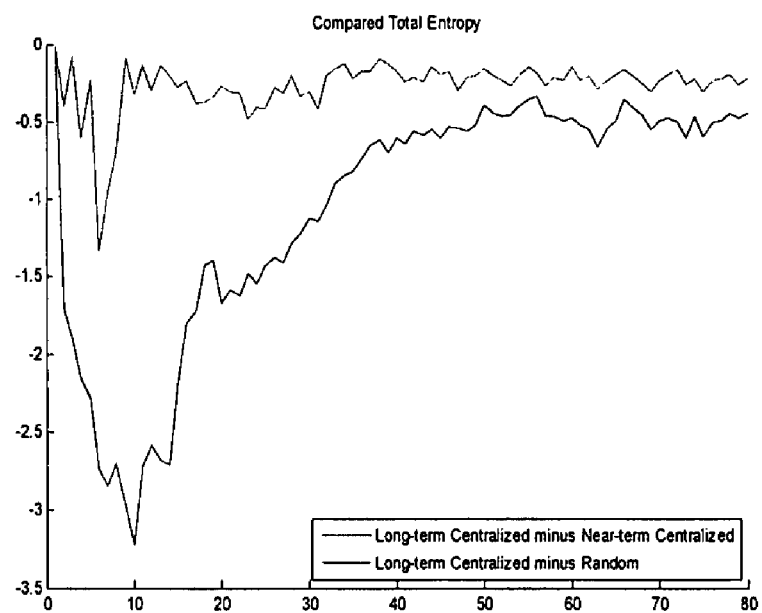
FIGS. 5a and 5b illustrate results of a first simulation example showing the performance improvement of the sparse sampling system of the present invention over a near term planner system.
Figure 5B:
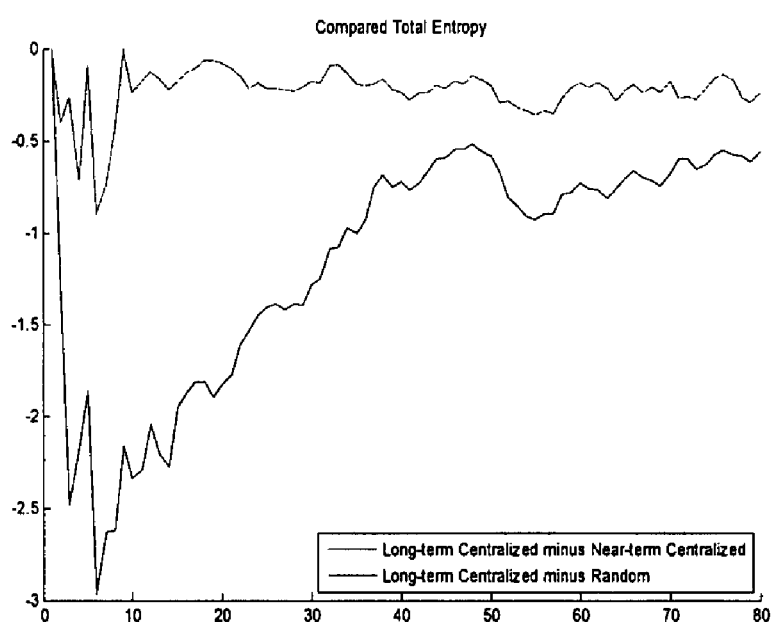

Results: Results were averaged over 50 Monte Carlo runs and are presented in FIG. 5a. As expected, the random planner performed worse than both the near-term and long-term planners. The long-term planner performed better than the near-term planner in both cases. One of the tracks crosses the blind spot at t=50 in the FIG. 5b and the results of this crossing can be seen. The long-term planner performed notably better at this crossing point. As seen in FIGS. 5a and 5b, the long-term planner needed lesser measurements to achieve the desired performance objective for all tracks much more quickly than the near-term planner. The actual quantitative difference between the two planners will depend on the problem size, desired goal and sensor characteristics.

Figure 6A:
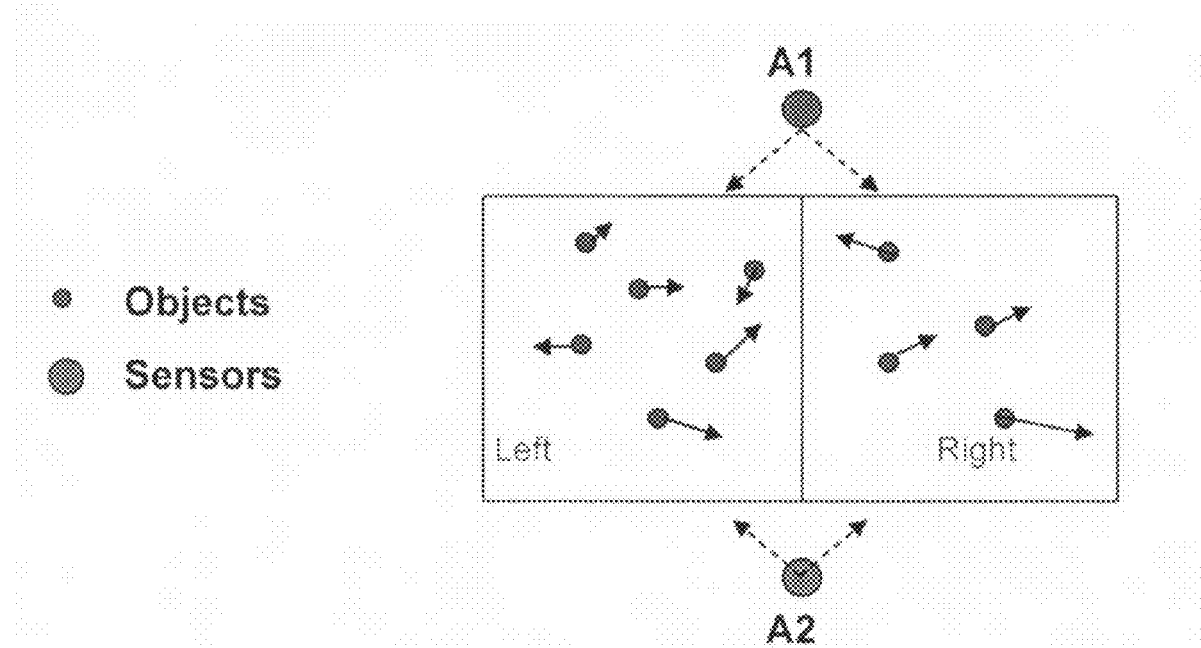
FIGS. 6a through 6c illustrate the results of a second simulation example showing the performance improvement of the sparse sampling system of the present invention over a near term planner system.

In another scenario, the simulation, 10 moving tracks in a 2 km×1 km surveillance region of interest with two zones—left half and right half (see FIG. 6a) were simulated. The system assumed two sensors, each of which could only look in one zone at each sampling instant and could provide both noisy kinematic and classification information for all tracks in that zone. The position measurement errors, sensor confusion matrix and costs were similar to the previous example. Again, the simulation compared the near-term and long-term planners. At each decision point, it was only possible to use both sensors but in only one zone (Left or Right). The purpose was to determine what control decision should be made at each decision point so as to maximize localization and classification accuracy of all objects with minimal sensing cost.

Figure 6B:
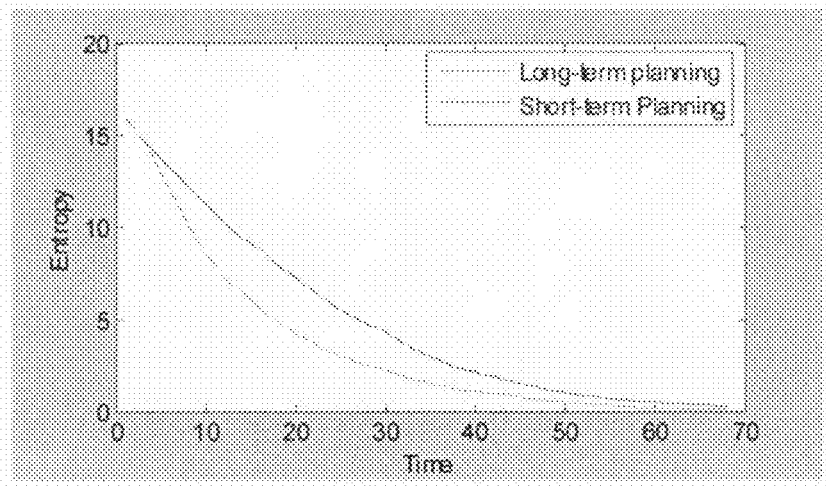
Figure 6C:
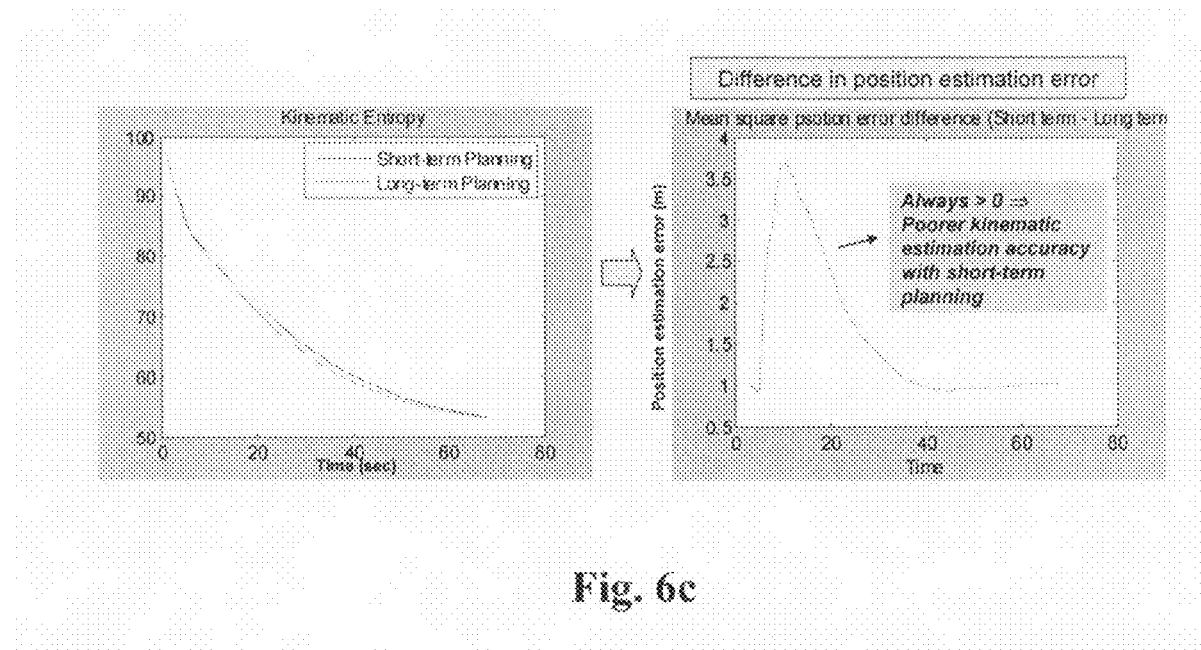

The simulation performed 50 Monte Carlo runs and plotted the average entropy results for classification and kinematic cases as shown below in FIGS. 6b through 6d. FIG. 6b illustrates a plot of classification entropy vs. time for near-term and long-term planners. FIG. 6c illustrates a plot of kinematic entropy vs. time for near-term and long-term planners. It can be seen from the figures that the classification and kinematic uncertainties reduced much faster for the long-term planner compared to the near-term planner indicating better sensor resource management for the same resources as the near-term planner.

From the above, it is seen how the method and system of the sparse sampling planner uses a finite number of measurements to determine a track's expected intermediate kinematic and classification state for a specific sensor action. It uses the expected track state to compute a reward function. The expected states are further propagated for actions at the next time step to determine the next states and so on. The sampling becomes sparse and the reward function is discounted as one propagates further in time. This produces a state-action tree that is more top-heavy while providing greater accuracy at times closer to the decision point. By doing so, the method and system creates a plan comprising a sequence of actions that result in the highest reward. By employing various heuristics to further prune the tree gives highly accurate results with significant savings in computational processor time.

REFERENCES

1. W. Schmaedeke, "Information Based Sensor Management," Signal Processing, Sensor Fusion, and Target Recognition II. Proceedings of the SPIE—The International Society for Optical Engineering, vol. 1955, Orlando, Fla., Apr. 12-14, 1993, pp. 156-64.
2. W. Schmaedeke and K. Kastella, "Information Based Sensor Management and IMMKF," Signal and Data Processing of Small Targets 1998: Proceedings of the SPIE—The International Society for Optical Engineering, vol. 3373, Orlando, Fla., April 1998, pp. 390-401.
3. K. Kastella, "Discrimination Gain to Optimize Detection and Classification," IEEE Transactions on Systems, Man, and Cybernetics, Part A: Systems and Humans, vol. 27, no. 1, pp. 112-116, January 1997.
4. G. A. McIntyre and K. J. Hintz, "An Information Theoretic Approach to Sensor Scheduling," Signal Processing, Sensor Fusion, and Target Recognition V. Proceedings of the SPIE—The International Society for Optical Engineering, vol. 2755, Orlando, Fla., Apr. 8-10 1996, pp. 304-312.
5. M. Kalandros and L. Y. Pao. "Covariance Control for Multisensor Systems," IEEE Trans. Aerospace Electronic Systems, vol. 38, No. 4, 2002.
6. V. Krishnamurthy, "Algorithms for optimal scheduling and management of hidden Markov model sensors," IEEE Trans. Signal Process. 50 (6) (2002) 1382-1397.
7. V. Krishnamurthy, D. Evans, "Hidden Markov model multiarm bandits: a methodology for beam scheduling in multitarget tracking," IEEE Trans. Signal Process. 49 (12) (2001) 2893-2908.
8. D. P. Bertsekas, D. Castanon, "Rollout algorithms for stochastic scheduling problems," J. Heuristics, 5 (1) (1999) 89-108.
9. R. Malhotra, "Temporal considerations in sensors management," Proceedings of the IEEE 1995 National Aerospace and Electronics Conference, NAECON, vol. 1, Dayton, Ohio, 22-26 May 1995, pp. 86-93.
10. K. J. Hintz, "A measure of the information gain attributable to cueing," IEEE Signal Process. Mag. (Special Issue on Math. Imaging) 19 (5) (2002) 85-95.
11. K. J. Hintz, E. S. McVey, "Multi-process constrained estimation," *IEEE Trans. Man Systems Cybernet.* 21 (1991) 237-244.
12. W. Schmaedeke, K. Kastella, "Event-averaged maximum likelihood estimation and information-based sensor management," *Proceedings of SPIE*, vol. 2232, Orlando, Fla., 1994, pp. 91-96.
13. R. E. Kalman, "A New Approach to Linear Filtering and Prediction Problems," *Transactions of the ASME—Journal of Basic Engineering,* 82(D), 35-45, 1960.
14. M. J. Kearns, Y. Mansour, and A. Y. Ng, "A Sparse Sampling Algorithm for Near-Optimal Planning in Large Markov Decision Processes," *Proceedings of the Sixteenth International Joint Conference on Artificial Intelligence*, T. Dean (Ed.), pp. 1324-1331, Morgan Kaufmann, 1999.

Glossary of Terms

1. A track is a time sequence of Kinematic measurements (position/velocity, class/ID (probability) search estimates for an object (target).

2. A sensor is used to measure characteristics of a target, including kinematic measurements, class measurements and search measurements.

3. A kinematic measurement is a measurement regarding some kinematic characteristic of a target, such as position and/or velocity. Kinematic measurements are typically generated through the use of a sensor such as a radar generating radar signals.

4. A class measurement is a measurement directly about the class/type of target or indirect measurement about the class/type in the form of features. A class is information about the object to be identified (e.g. whether the object is a tank or truck). A feature, generally, is a frequency of a signal from the object (represents a characteristic or attribute). The latter generally assumes that some relationship between features and the class (type) are available in the form of uncertainty rules.

5. Multi-sensor data fusion is the combining of sensory data or data derived from sensory data form disparate sources (e.g. sensors (radar)) such that the resulting information is in some sense better (e.g. more accurate, more complete or more dependable) that would be possible when these sources were used individually.

6. A Kalman filter is an efficient recursive filter which estimates the state of a dynamic system from a series of incomplete and noisy measurements. An example of an application would be to provide accurate continuously-updated information about the position and velocity of an object given only a sequence of observations about its position, each of which includes some error. The Kalman filter is recursive which means that only the estimated state from the previous time step and the current measurement are needed to compute the estimate for the current state 7. A tracker is a component of a radar system that aggregates individual radar observations into tracks. It is particularly useful when the radar system is reporting data from several different targets. A tracker operates by comparing the incoming data from the radar sensor with earlier data and determining which new observations are consistent with existing tracks. A typical tracker employs a Kalman filter or a similar device to make the comparison. Depending on the particular data produced by the sensor, the tracker may use a sequence of the target's reported locations to deduce the target's course and speed, or it may use the reported course and speed to aid in tracking.

8. Synthetic aperture radar (SAR) is a form of radar in which sophisticated post-processing of radar data is used to produce a very narrow effective beam and allows broad area imaging at high resolutions.

9. Search SAR mode is generally defined as a mode in which the radar/tracking system is capable of providing low accuracy information for stationary target information over a broad area.

10. Spot SAR mode is generally defined as a mode in which the radar/tracking system is capable of providing more accurate information for stationary targets but over a smaller area than Search SAR. The spot SAR mode provides very high-resolution images of fixed targets from an airborne platform, while the Search SAR mode provides wide-area fixed target imagery.

11. GMTI (Ground Moving Target Indicator) mode is generally defined as a mode in which the radar/tracking system is capable of providing target location and velocity profiles;

12. SIGINT mode is generally defined stands for SIGnals INTelligence, which is intelligence-gathering by interception of signals, whether by radio interception or other means.

13. A knowledge base is a special kind of database for knowledge management. It provides the means for the computerized collection, organization, and retrieval of knowledge in the present system in the form of sensor modes and capabilities, the type of tracker being used and type of classifier. It would also contain track files, data quality reports, confidence reports with attribute information. As stated, the knowledge base contains information about sensors, their capabilities, and operational modes. For example, it may list that sensor 1 can operate in Search SAR and Spot SAR modes and list the measurement accuracies of these operational modes. It may also list the maximum FOV of the sensor, the maximum speed and turn rate of the sensor platform, etc. It may also list the type of kinematic tracker (e.g., standard Kalman filter) and ID engine (e.g., standard Bayesian classifier) to be used in the system. The information contained in the knowledge base is used to determine the various sensor options and information gain values for a track or cell.

14. Performance Requirements are the desired goals to be achieved by the system. The desired kinematic performance goal state is usually specified as desired kinematic track accuracy. For example, the desired tracking accuracy of an incoming target in various phases may be as follows:

| | |
|---|---|
| Tracking accuracy - Maintenance | 20 m |
| Tracking accuracy - Mid-course | 10 m |
| Tracking accuracy - Terminal | 2 m |

The above numbers represent the rms tracking accuracy value in meters.

The system translates the desired goal "kinematic" accuracy into a desired goal "information" state. One interpretation used in this embodiment is to translate desired goal "kinematic" accuracy into a desired goal covariance entropy value.

EXAMPLE

Goal mid-course tracking accuracy=10 m

Current kinematic accuracy (square root of variance) of Track 1=75 m

Information Needs of Track 1=Differential entropy between current and goal states=3.165.

15. Shannon entropy or information entropy is a measure of the uncertainty associated with a discrete random variable. It is a measure of the average information content the recipient is missing when they do not know the value of the random variable. In information theory, self-information is a measure of the information content associated with the outcome of a discrete random variable. It is expressed in the unit of information: the bit. By definition, the amount of self-information contained in a probabilistic event depends only on the probability p of that event. More specifically: the smaller this probability is, the larger is the self-information associated with receiving information that the event indeed occurred.

16. Differential entropy (also referred to as continuous entropy) is a concept in information theory which tries to extend the idea of (Shannon) entropy, a measure of average surprisal of a random variable, to continuous probability.

17. Covariance matrix in statistics and probability theory, is a matrix of covariances between elements of a vector. It is the natural generalization to higher dimensions of the concept of the variance of a scalar-valued random variable. Intuitively, covariance is the measure of how much two random variables vary together (as distinct from variance, which measures how much a single variable varies). If the two variables are independent, then their covariance is zero.

18. A confusion matrix is a visualization tool typically used in supervised learning (machine learning technique for creating a function from training data). In unsupervised learning, it is typically called a matching matrix. Each column of the matrix represents the instances in a predicted class, while each row represents the instances in an actual class. One benefit of a confusion matrix is that it is easy to see if the system is confusing two classes (i.e. commonly mislabelling one as an other). Also, unsupervised learning is a method of machine learning where a model is fit to observations. It is distinguished from supervised learning by the fact that there is no a priori output. In unsupervised learning, a data set of input objects is gathered. Unsupervised learning then typically treats input objects as a set of random variables. A joint density model is then built for the data set. Unsupervised learning can be used in conjunction with Bayesian inference to produce conditional probabilities (i.e. supervised learning) for any of the random variables given the others.

19. Bayesian engine or Bayes estimator in decision theory and estimation theory, is an estimator or decision rule that maximizes the posterior expected value of a utility function or minimizes the posterior expected value of a loss function. Specifically, suppose an unknown parameter θ is known to have a prior distribution Π. Let δ be an estimator of θ (based on some measurements), and let R(θ,δ) be a risk function, such as the mean squared error. The Bayes risk of δ is defined as $E_\Pi\{R(\theta,\delta)\}$, where the expectation is taken over the probability distribution of θ. An estimator δ is said to be a Bayes estimator if it minimizes the Bayes risk among all estimators.

20. A geographical state vector specifies the position and velocity of an object in space. There are state vectors for both kinematic and classification states for kinematic case, a simple embodiment is position and velocity information. For classification, a simple embodiment would be a probability vector comprising of probabilities of all possible class of that target, (e.g. If a target can possible be one of class C1, C2 of C3, then a class state vector could be [0.9 0.07 0.03] indicating probabilities of C1, C2 and C3.

21. An attribute is an entity that defines a property of an object, element, or file.

22. Monte Carlo run is used when there are variabilities in noise, sensor measurements, etc. wherein a large number of runs of the algorithm are carried out and used to plot the statistical quantities/results corresponding to these runs.

23. Data fusion is the combining of sensory data or data derived from sensory data from disparate sources such that the resulting information is in some sense better than would be possible when these sources were used individually. The term "better" in that case can mean more accurate, more complete, or more dependable, or refer to the result of an emerging view, such as stereoscopic vision (calculation of depth information by combining two-dimensional images from two cameras at slightly different viewpoints). The data sources for a fusion process are not specified to originate from identical sensors. One can distinguish direct fusion, indirect fusion and fusion of the outputs of the former two. Direct fusion is the fusion of sensor data from a set of heterogeneous or homogeneous sensors, soft sensors, and history values of sensor data, while indirect fusion uses information sources like a priori knowledge about the environment and human input. Sensor fusion is also known as (multi-sensor) data fusion and is a subset of information fusion.

24. Cost horizon is the number of time slots (samples) to produce a plan for the number of step planning horizon for different number of objects.

25. Reward is the relative gain computed.

26. Seeding is the process of starting from a given state.

27. Current track picture means the same as current track kinematic and classification states.

29. Action tree or state-action tree is a sequence of sensor actions (e.g. which mode, where they look, etc.) or chains of actions.

30. Cumulative rate is the sum of rates.

While the invention has been shown and described with reference to specific preferred embodiments, it should be understood by those skilled in the art that various changes in form and detail may be made therein without departing from the spirit and scope of the invention as defined by the following claims.

What is claimed is:

1. A sparse sampling planner method for providing a plan for long term management of a system of multiple sensors that operates to observe a plurality of tracks/targets wherein each sensor has a number of characteristics including different operational modes and viewing geometries settings, each operational mode incurring cost and providing different information about the tracks, the method comprising the steps of:

(a) receiving current track kinematic and classification state inputs representative of a current track picture from a fusion module of the system which receives kinematic and classification measurements of the targets from the multiple sensors during a measurement cycle and performance requirements inputs from a performance data file;

(b) beginning with a single root node corresponding to a given state, computing the information need from the inputs of step (a) for generating kinematic and classification information need entropy outputs in terms of a common metric for obtaining an overall value of information need, if the information need of any track is less than or equal to zero, disregard the track for planning purposes;

(c) using a generator model, generating sensor action combinations as a permutation of all possible sensor viewing geometries and operational modes;

(d) using a sparse sampling planner simulator, generating a predetermined number of samples simulating several measurements of a track for each action resulting in total number of nodes for that sensor defined by the number of sensor modes, the number of viewable geometries and a discount factor value at a current depth corresponding to a layer of a state-action tree structure;

(e) reducing the number of sensor action nodes by implementing thresholding for eliminating certain sensor action combinations;

(f) for each of the remaining sensor action nodes determined in step (e), computing the value of information gain generated in terms of the common metric of step (b) corresponding to the difference between information gain entropy output of the node from which the node was generated and the information gain entropy output of the remaining node and a reward value corresponding to the rate of information gain;

(g) storing a cost value denoting the cost of the sensor action and summing the cost value for each sensor action computed in step (f);

(h) repeating the operations of steps (b) and (c) recursively until the cumulative cost value in step (g) reaches a pre-established cost horizon value ending further generation of the action tree structure;

(i) determining the value of each chain of actions along the action tree structure by averaging the information gain values of all samples along that chain; and, (j) selecting the chain of actions having the best gain value for carrying out the long term management of the multiple sensors.

2. The method of claim 1 further comprising the step of executing the first action in the selected chain of actions for collecting sensor measurements using the selected first action.

3. The method of claim 2 further comprising the step of repeating the planning process defined by steps (a) through (i) until all track information needs computed in step (b) less than or equal to zero indicating that all performance goals have been reached.

4. The method of claim 1 wherein in step (b), kinematic information need and classification information need respectively are computed according to the following expressions:

$$N_t(X) = H_{before}(X) - H_d(X) = \log_2\left(\frac{|P_{before}|}{|P_d|}\right) \text{ and,}$$

$$N_t(C) = H_t(C) - H_{t,d}(C).$$

5. The method of claim 1 wherein in step (f) the total gain is computed as the difference in entropy output between classification information gain and kinematic information gain given by the following expression:

$$\Delta h(t) = \sum_{i=1}^{N} (h_S(b^i(t)) - h_S(b^i(t+1))) +$$

$$\alpha \sum_{i=1}^{N} (h_D(P^i(t|t)) - h_D(P^i(t+1|t+1)))$$

wherein $h_S$=Shannon entropy value, $h_D$=differential entropy value, b=belief state, P=covariance matrix and a is a parameter used for scaling the importance of kinematic gain and classification (identification) information gain.

6. The method of claim 5 wherein in step (f) the rate of information gain (RIG) is computed using the results of claim 5 according to the following expression:

$$RIG(t) = \frac{\Delta h(t)}{c_t}$$

wherein $c_t$ is the deterministic cost at time t.

7. The method of claim 1 wherein in step (c) the number of sensor action combinations is defined by the following expression:

$$N = (mv)^s$$

where m=the number of sensor modes, v=the number of viewing geometries and s=the number of sensors.

8. The method of claim 1 wherein in step (d), the sparse sampling planner generates the predetermined number S of samples according to the following expression:

$$S = \gamma^d$$

wherein γ is a discount factor value, w=the number of samples at the lowest look-ahead depth, and d=the current depth for generating a total number of nodes equal to $m^s v^s \gamma^d$ at the current depth where $(mv)^s$ equals the number of action combinations and $\gamma^d$ equals the discount factor value.

9. The method of claim 1 wherein step (e) utilizes an n-best thresholding method for reducing the number of nodes in which only the n actions with the highest one-step expected rates of gain are considered reducing the number of calls to the generator model of step (c).

10. The method of claim 1 wherein step (e) utilizes an a thresholding method in which the parameter a controls what actions are considered so that the maximum overall actions of the expected one-step values at least ax max are considered, otherwise, the actions with expected one-step values of at least max/a are considered.

11. The method of claim 1 wherein if the cost horizon is exceeded, then step (h) further includes the step of interpolating the gain and cost values of the particular sensor action.

12. A multisensor system including sparse sampling planner module for providing a plan for long term management of multiple sensors, the system including a fusion module operatively coupled to the multiple sensors for receiving kinematic and classification measurements during a measurement cycle and an information needs module operatively coupled to the fusion module for receiving current track kinematic and classification state inputs representative of a current track picture and performance inputs, the multiple sensors being operative to observe a plurality of tracks/targets wherein each sensor has a number of characteristics including different operational modes and viewing geometries settings, each operational mode incurring cost and providing different information about the tracks, the planner module comprising:

(a) inputs for receiving from the fusion module, signals corresponding to the current kinematic and classification states;

(b) a need compute module which is operative starting with a single root node corresponding to a given state, to compute the information need from the inputs for generating kinematic and classification information need entropy outputs in terms of a common metric for obtaining an overall value of information need of a track and operative if the information need of any track is less than or equal to zero to disregard the track for planning purposes;

(c) a generator model component for generate sensor action combinations as a permutation of all possible sensor viewing geometries and operational modes;

(d) a sparse sampling planner simulator component for generating a predetermined number of samples simulating several measurements of a track for each action resulting in total number of nodes for that sensor defined by the number of sensor modes, the number of viewable geometries and a discount factor value at a current depth corresponding to a portion or layer of a state-action tree structure;

(e) a thresholding component in response to the planner component, operating to reduce the number of sensor action nodes by for eliminating certain sensor action combinations;

(f) an information gain compute component operative for each of the remaining sensor action nodes to compute the value of information gain generated in terms of the common metric of step (b) corresponding to the difference between information gain entropy output of the node from which the node was generated and the information gain entropy output of the remaining nodes and computing a reward value corresponding to the rate of information gain, the gain compute component including storage for storing a cost value denoting the cost of the sensor action and summing the cost value for each sensor action computed by the gain compute module;

(g) the information need module and generator model component repeating their operations) recursively until the cumulative cost value generated by the information gain component reaches a pre-established cost horizon value ending further generation of the state-action structure; and, (h) the information gain component being operative to determine the value of each chain of actions along the action tree structure by averaging the information gain values of all samples along that chain; and being operative to select the chain of actions having the best gain value for carrying out the long term management of the multiple sensors.

13. The system of claim 12 wherein the particular sensor executing the first action in the selected chain of actions for collecting sensor measurements using the selected first action.

14. The system of claim 12 wherein the planner module operates to repeat the operations being carried out by the components until all track information needs computed by the information needs module is less than or equal to zero indicating that all performance goals have been reached.

15. The system of claim 12 wherein the kinematic information need and classification information need respectively computed by the information needs module are computed according to the following expressions:

$$N_t(X) = H_{before}(X) - H_d(X) = \log_2\left(\frac{|P_{before}|}{|P_d|}\right) \text{ and,}$$

$$N_t(C) = H_t(C) - H_{t,d}(C).$$

16. The system of claim 12 wherein the information gain module computes the total gain as the difference in entropy output between classification information gain and kinematic information gain given by the following expression:

$$\Delta h(t) = \sum_{t=1}^{N} (h_S(b^j(t)) - h_S(b^j(t+1))) +$$

-continued $$\alpha \sum_{i=1}^{N} (h_D(P^i(t|t)) - h_D(P^i(t+1|t+1)))$$

wherein $h_s$=Shannon entropy value, $h_D$=differential entropy value, b=belief state, P=covariance matrix and a is a parameter used for scaling the importance of kinematic gain and classification (identification) information gain.

17. The system of claim 16 wherein the information gain module computes a reward value corresponding to the rate of information gain (RIG) using the results of claim 16 according to the following expression:

$$RIG(t) = \frac{\Delta h(t)}{c_t}$$

wherein $c_t$ is the deterministic cost at time t.

18. The system of claim 12 wherein generator model component computes the number of sensor action combinations according to the following expression:

$$N=(mv)^s$$

where m=the number of sensor modes, v=the number of viewing geometries and s=the number of sensors.

19. The system of claim 12 wherein the sparse sampling planner generates the predetermined number S of samples according to the following expression:

$$S=\gamma^d$$

wherein $\gamma$ is a discount factor value, w=the number of samples at the lowest look-ahead depth, and d=the current depth for generating a total number of nodes equal to $m^s v^s \gamma^d$ at the current depth where $(mv)^s$ equals the number of action combinations and $\gamma^d$ equals the discount factor value.

20. The system of claim 12 wherein the thresholding component utilizes an n-best thresholding method for reducing the number of nodes in which only the n actions with the highest one-step expected rates of gain are considered reducing the number of calls to the generator model component.

21. The system of claim 12 wherein the thresholding component utilizes an a thresholding method in which the parameter a controls what actions are considered so that the maximum overall actions of the expected one-step values at least ax max are considered, otherwise, the actions with expected one-step values of at least max/a are considered.

22. The system of claim 12 wherein if the cost horizon is exceeded, then the information gain module operates to scale the gain and cost values of the particular sensor action.

23. A sparse sampling planner program product for providing a plan for long term management of multiple sensors of a system that operates to observe a plurality of tracks/targets wherein each sensor has a number of characteristics including different operational modes and viewing geometries settings, each operational mode incurring cost and providing different information about the tracks, the program product comprising:
(a) a first set of routines for receiving current track kinematic and classification state inputs representative of a current track picture from a fusion module of the system which receives kinematic and classification measurements of the targets from the multiple sensors during a measurement cycle and performance requirements inputs from a performance data file;
(b) a second set of routines operative beginning with a single root node corresponding to a given state, to compute the information need from the inputs of step (a) for generating kinematic and classification information need entropy outputs in terms of a common metric for obtaining an overall value of information need, if the information need of any track is less than or equal to zero, disregard the track for planning purposes;
(c) a third set of routines including a generator model for generating sensor action combinations as a permutation of all possible sensor viewing geometries and operational modes;
(d) a forth set of routines including a sparse sampling planner simulator operative to generate a predetermined number of samples simulating several measurements of a track for each action resulting in total number of nodes for that sensor defined by the number of sensor modes, the number of viewable geometries and a discount factor value at a current depth corresponding to a layer of a state-action tree structure;
(e) a fifth set of routines including a thresholding function operative to reduce the number of sensor action nodes by eliminating certain sensor action combinations;
(f) a sixth set of routines for computing the value of information gain for each of the remaining sensor action nodes determined by the fifth set of routines in terms of the common metric used by the second set of routines corresponding to the difference between information gain entropy output of the node from which the node was generated and the information gain entropy output of the remaining node, the sixth set of routines including routines for computing a reward value corresponding to the rate of information gain and for storing a cost value denoting the cost of the sensor action and summing the cost value for each sensor action computed;
(h) a seventh set of routines operative to repeat the operations performed by the second and third set of routines recursively until the cumulative cost value obtained by the sixth set of routines reaches a pre-established cost horizon value ending further generation of the state-action structure; and,
(i) an eighth set of routines being operative to determine the value of each chain of actions along the action tree structure by averaging the information gain values of all samples along that chain; and, select the chain of actions having the best gain value for carrying out the long term management of the multiple sensors.

24. The program product of claim 23 wherein the particular sensor operates to execute the first action in the selected chain of actions for collecting sensor measurements using the selected first action.

25. The program product of claim 23 further comprising a further routine causing the repeating the planning operations by the planning module routines until all track information needs computed by the second set of routines is less than or equal to zero indicating that all performance goals have been reached.

* * * * *